United States Patent
Yoshioka et al.

(10) Patent No.: US 8,692,982 B2
(45) Date of Patent: Apr. 8, 2014

(54) METHOD FOR OBSERVING FLUID AND FLUID FLOW OBSERVATION

(75) Inventors: Kunihiko Yoshioka, Nagoya (JP); Satoshi Ishibashi, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 390 days.

(21) Appl. No.: 13/022,848

(22) Filed: Feb. 8, 2011

(65) Prior Publication Data
US 2011/0199603 A1 Aug. 18, 2011

(30) Foreign Application Priority Data
Feb. 12, 2010 (JP) ................... 2010-029043

(51) Int. Cl.
G01P 3/36 (2006.01)

(52) U.S. Cl.
USPC ............................. 356/28; 356/28.5

(58) Field of Classification Search
USPC .................................. 356/28, 28.5
See application file for complete search history.

(56) References Cited

U.S. PATENT DOCUMENTS

| | | | |
|---|---|---|---|
| 4,664,513 A | 5/1987 | Webb et al. | |
| 5,131,741 A * | 7/1992 | Zweben | 356/28 |
| 6,118,519 A | 9/2000 | Ipponmatsu et al. | |
| 6,211,956 B1 * | 4/2001 | Nicoli | 356/337 |
| 6,414,748 B1 | 7/2002 | Ipponmatsu et al. | |
| 6,903,812 B2 | 6/2005 | Ipponmatsu et al. | |
| 2005/0084423 A1 * | 4/2005 | Zarowitz et al. | 422/100 |
| 2005/0219507 A1 | 10/2005 | Ipponmatsu et al. | |
| 2008/0003176 A1 | 1/2008 | Sasaki et al. | |
| 2008/0008645 A1 | 1/2008 | Sasaki et al. | |
| 2008/0031807 A1 | 2/2008 | Sasaki et al. | |
| 2009/0208651 A1 | 8/2009 | Oyanagi et al. | |

FOREIGN PATENT DOCUMENTS

| | | |
|---|---|---|
| EP | 1 033 347 A1 | 9/2000 |
| EP | 1 136 461 A2 | 9/2001 |
| EP | 2 048 508 A2 | 4/2009 |
| JP | 55-141072 U | 10/1980 |
| JP | 05-052861 A1 | 3/1993 |
| JP | 08-313549 A1 | 11/1996 |
| JP | 2003-084005 A1 | 3/2003 |
| JP | 2005-040299 A1 | 2/2005 |
| WO | 99/11574 A1 | 3/1999 |

OTHER PUBLICATIONS

Extended European Search Report dated Jul. 9, 2013.

* cited by examiner

*Primary Examiner* — Luke Ratcliffe
(74) *Attorney, Agent, or Firm* — Burr & Brown, PLLC

(57) ABSTRACT

A fluid observation apparatus for performing a method for observing a fluid by PIV. The method for observing a fluid includes capturing an image of inorganic particles in a fluid for flow observation by irradiating the fluid for flow observation passing through a flow channel with light, the fluid for flow observation containing inorganic particles to be observed each having a planar surface, a dispersion medium to be observed, and a viscosity modifier. The fluid for flow observation is high-viscosity non-Newtonian slurry containing inorganic particles. The fluid for flow observation may be a simulated fluid for a fluid for flow analysis. The simulated fluid closely resembles the particle size of inorganic particles to be analyzed and the viscosity of the fluid for flow analysis. The fluid for flow analysis contains the inorganic particles to be analyzed and a dispersion medium to be analyzed.

15 Claims, 4 Drawing Sheets

METHOD FOR OBSERVING FLUID AND FLUID FLOW OBSERVATION

BACKGROUND OF THE INVENTION

1. Field of the Invention

The present invention relates to a method for observing a fluid and a fluid for flow observation.

2. Description of the Related Art

Heretofore, particle image velocimetry (hereinafter referred to as PIV) has been used as a method for observing a fluid. Particle image velocimetry involves adding particles following the flow (tracer particles) to the fluid, irradiating the fluid with a pulsed laser beam to track the movement of the fluid, following the motion of the tracer particles with a video camera or the like, capturing images of the travel distance of the particles at sufficiently small time intervals on a flow time scale, and determining the distance and direction of the travel (see, for example, Japanese Unexamined Patent Application Publication No. 2003-84005).

SUMMARY OF THE INVENTION

Fluids can be classified into Newtonian fluids, the viscosity of which is independent of shear rate and time, and non-Newtonian fluids, the viscosity of which is dependent on shear rate and time. For example, slurries containing a large number of inorganic particles are non-Newtonian fluids. Slurries containing inorganic particles are mostly opaque. It is therefore difficult to observe the interior of slurry. The addition of tracer particles merely allows the observation of the surface of slurry. A method for observing a fluid described in Japanese Unexamined Patent Application Publication No. 2003-84005 does not take such a fluid into account and cannot successfully observe the movement of particles in fluids containing inorganic particles.

In view of the problems described above, the present invention can ensure the observation of the movement of a fluid containing inorganic particles. Accordingly, it is a principal object of the present invention to provide a method for observing a fluid and a fluid for flow observation.

As a result of diligent research to achieve the principal object, the present inventors completed the present invention by finding that the movement of a fluid containing inorganic particles can be observed with higher reliability by adding inorganic particles each having a planar surface to the fluid and irradiating the fluid with light.

A method for observing a fluid according to one aspect of the present invention is a method for observing a fluid by particle image velocimetry (PIV), including a capturing step of capturing an image of inorganic particles in a fluid for flow observation by irradiating the fluid for flow observation passing through a flow channel with light. The fluid for flow observation contains inorganic particles to be observed each having a planar surface, a dispersion medium to be observed, and a viscosity modifier.

A fluid for flow observation according to one aspect of the present invention is a fluid for flow observation to be observed by PIV. The fluid contains inorganic particles to be observed each having a planar surface, a dispersion medium to be observed, and a viscosity modifier.

A method for observing a fluid and a fluid for flow observation according to the present invention can ensure the observation of the movement of a fluid containing inorganic particles. This is because the fluid for flow observation contains a dispersion medium to be observed and a viscosity modifier for adjusting the fluid viscosity. The concentration of inorganic particles can be controlled via the dispersion medium, and the viscosity of the fluid can be controlled via the viscosity modifier. These can increase the translucency of the fluid. Furthermore, the fluid for flow observation contains inorganic particles to be observed each having a planar surface. Upon light irradiation, it is assumed that the planar surfaces block or reflect light, thereby improving the visibility of the particles. This can ensure the observation of the movement of the fluid containing the inorganic particles. In addition to the inorganic particles to be observed each having a planar surface, the fluid for flow observation may further contain inorganic particles to be observed not having a planar surface.

DETAILED DESCRIPTION OF THE INVENTION

Figure 1:
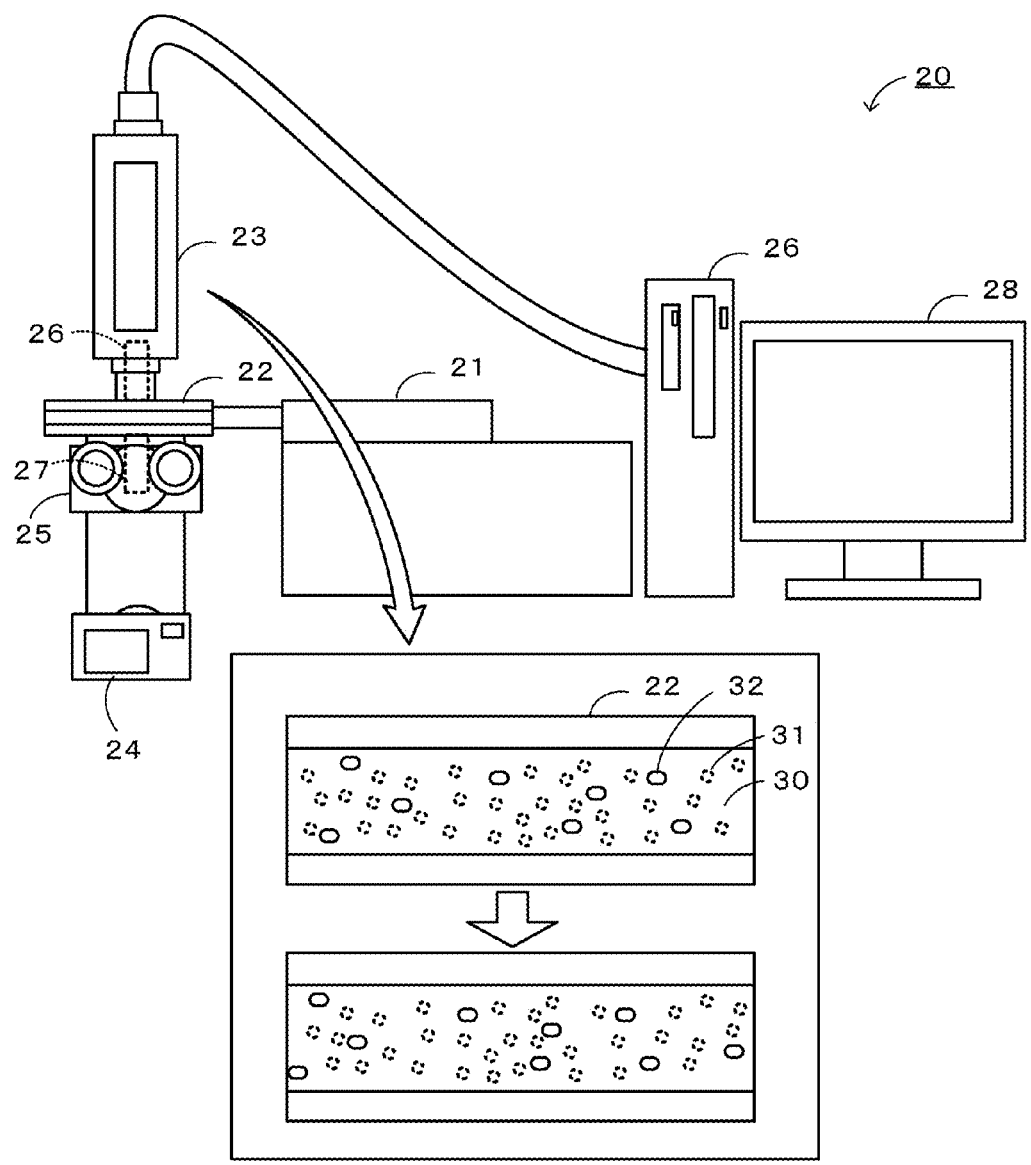
FIG. 1 is a schematic view of a fluid observation apparatus 20 according to an embodiment of the present invention.

Embodiments of the present invention will be described below with reference to the drawings. FIG. 1 is a schematic view of a fluid observation apparatus 20 according to an embodiment of the present invention. The fluid observation apparatus 20 is an observation apparatus with which a method for observing a fluid according to the present invention is performed. The fluid observation apparatus 20 includes a fluid supply unit 21, with which the feed rate of a fluid can be controlled, and a transmission cell 22 made of a transparent member through which the fluid passing through can be observed. The fluid observation apparatus 20 further includes a digital video camera 23 for capturing motion pictures of the fluid disposed over the transmission cell 22, a digital camera 24 for capturing still pictures of the fluid disposed under the transmission cell 22, and a microscope 25, which can magnify the fluid for visual recognition. The fluid observation apparatus 20 further includes photoirradiation units 26 and 27 for irradiating the transmission cell 22 with light from above and below, respectively. A fluid for flow observation 30 to be observed is supplied from the fluid supply unit 21 to the transmission cell 22, in which the movement of the fluid is observed. The fluid for flow observation 30 will be described below.

The fluid for flow observation 30 according to an embodiment of the present invention is a slurry containing inorganic particles. The slurry contains the inorganic particles to be observed, a dispersion medium to be observed, and a viscosity modifier. The fluid for flow observation 30 is a non-Newtonian fluid that contains generally spherical inorganic particles 31 and planar inorganic particles 32 each having a planar surface. The inorganic particles 31 and the planar inorganic particles 32 are hereinafter collectively referred to as inorganic particles to be observed. When the fluid for flow observation 30 is irradiated with light, the planar surfaces of the planar inorganic particles 32 facilitate the formation of shaded images or reflected images, thereby facilitating the observation of the movement of the inorganic particles. Furthermore, use of the viscosity modifier for adjusting the fluid viscosity can reduce the number of inorganic particles to be observed and thereby increase the translucency of the fluid, facilitating the observation of the movement of the inorganic particles.

Examples of the inorganic particles to be observed contained in the fluid for flow observation 30 include ceramic particles, metal particles, glass particles, and at least two selected therefrom. Examples of the ceramic particles include particles made of alumina, zirconia, yttrium-aluminum-garnet (YAG), oxides and complex oxides of Al, Zr, Mg, Y, Sc, La, Si, Na, Cu, Fe, Ca, Ni, Li, Mn, Gd, Ce, Hf, Ti, Pb, Ba, and Nb, carbide, such as silicon carbide, nitrides, such as aluminum nitride and silicon nitride, and mixtures thereof. Examples of the metal particles include particles made of transition metals, such as molybdenum and tungsten, noble metals, such as gold, silver, and platinum, and alloys thereof. Examples of the glass particles include quartz particles and borosilicate particles. Preferably, the purities of the components of the inorganic particles are 90% or more. The inorganic particles each having a planar surface can be manufactured by crushing a product formed and fired.

The dispersion medium to be observed contained in the fluid for flow observation 30 may be any dispersion medium that can dissolve a dispersing aid and a binder. Examples of the dispersion medium include water, hydrocarbons (such as toluene, xylene, and solvent naphtha), ethers (such as ethylene glycol monoethyl ether, butyl carbitol, and butyl carbitol acetate), alcohols (such as isopropanol, 1-butanol, ethanol, 2-ethylhexanol, terpineol, ethylene glycol, and glycerin), ketones (such as acetone and methyl ethyl ketone), esters (such as butyl acetate, dimethyl glutarate, and triacetin), and polybasic acids (such as glutaric acid). The dispersion medium may be preferably a mixture of aliphatic polyvalent ester and polybasic acid ester. The dispersion medium preferably contains 20 or less carbon atoms in terms of low viscosity.

The viscosity modifier contained in the fluid for flow observation 30 may be any viscosity modifier that can adjust the viscosity of the fluid for flow observation 30 and may be a dispersing aid or a binder. A dispersing aid used as the viscosity modifier can reduce the viscosity of the fluid for flow observation 30. A binder used as the viscosity modifier can increase the viscosity of the fluid for flow observation 30. Examples of the dispersing aid used as the viscosity modifier include sorbitan fatty acid esters, polycarboxylic acid copolymers, polymerized phosphate ester(salt) compounds, polymerized alkylammonium salt compounds having an acid group, and sodium alkylbenzenesulfonate. Examples of the binder used as the viscosity modifier include cellulose derivatives (such as methylcellulose, carboxy methylcellulose, and ethylcellulose), starch, polyvinyl alcohol, polyethylene glycol, butyral resin, acrylic resin, polyamide resin, and isocyanates (such as tolylene diisocyanate, diphenylmethane diisocyanate, and polyisocyanate).

The fluid for flow observation 30 may be a slurry for use in a gel casting process, in which a slurry containing inorganic particles and organic compounds is poured into a mold, is solidified by a chemical reaction between the organic compounds, for example, between a dispersion medium and a gelling agent or between gelling agents, and is removed from the mold. Thus, the dispersion medium to be observed may be a resin curable under predetermined conditions. This allows the flowability of slurry within the mold in the gel casting process to be examined. Examples of the resin curable under predetermined conditions include resin curable with a curing agent, resin curable by heating, and resin curable by ultraviolet irradiation.

The fluid for flow observation 30 may be a simulated fluid for flow observation closely resembling the particle size of inorganic particles to be analyzed and the viscosity of the fluid for flow analysis. The fluid for flow analysis contains the inorganic particles to be analyzed and a dispersion medium to be analyzed. If a fluid for flow analysis: the has a flow state of which is to be analyzed, having a low light transparency or reflectivity, the behavior of the fluid may be observed by using a fluid for flow observation 30 having a similar particle size and a similar viscosity as an alternative fluid. Thus, when the interior of a fluid containing inorganic particles cannot be observed, the interior of a fluid can be observed in a simulated manner. Since slurry within a mold in the gel casting process has a relatively low flow rate and a relatively large viscosity, the effects of inertial force are negligible. The density of inorganic particles related to the density of a fluid is therefore negligible. Thus, in the gel casting process, it is assumed that the behavior of slurries does not change significantly as long as the slurries have similar viscosities even if inorganic particles in the slurries have different densities. Thus, a fluid for flow analysis can be easily replaced with a simulated fluid for flow observation. The inorganic particles to be analyzed and the inorganic particles to be observed may be formed of the same material or different materials, preferably the same material. Likewise, the dispersion medium to be analyzed and the dispersion medium to be observed may be formed of the same material or different materials, preferably the same material. The particle size, as used herein, refers to the median particle size (D50) as determined by a laser diffraction method. The volume percentage of the inorganic particles to be observed in the fluid for flow observation 30 may be smaller than the volume percentage of the inorganic particles to be analyzed in the fluid for flow analysis to be analyzed. This can further increase the translucency of the fluid for flow observation 30. Even at a smaller volume percentage of the inorganic particles to be observed, the viscosity modifier can adjust the viscosity of the fluid for flow observation 30 to the fluid for flow analysis. The inorganic particles to be analyzed may be zirconia particles, and the inorganic particles to be observed may be silicon carbide particles. Thus, although shaded images or reflected images of zirconia particles are difficult to obtain, the fluid behavior of zirconia particles can be observed by using silicon carbide particles.

The volume percentage of the inorganic particles to be observed in the fluid for flow observation 30 is preferably 20% by volume or more and 40% by volume or less, more preferably 25% by volume or more and 35% by volume or less, of the volume of the slurry. At a volume percentage of 20% by volume or more, the number of inorganic particles is sufficient to observe the behavior of the inorganic particles. At a volume percentage of 40% by volume or less, light can easily pass through the fluid, and it is easy to observe the behavior of the inorganic particles within the fluid.

The fluid for flow observation 30 preferably has a viscosity of 10,000 (mPa·s) or more and 15,000 (mPa·s) or less, more preferably 11,000 (mPa·s) or more and 14,000 (mPa·s) or less, as measured with a B type viscometer at a number of revolutions of 1.5 rpm. These ranges are close to, for example, the viscosity of slurry in the gel casting process, allowing the observation of inorganic particles in the slurry. The fluid for flow observation 30 preferably has a viscosity of 6,000 (mPa·s) or more and 10,000 (mPa·s) or less, more preferably 7,000 (mPa·s) or more and 9,000 (mPa·s) or less, as measured with a B type viscometer at a number of revolutions of 3.0 rpm.

In the measurement with a B type viscometer, when $\eta x$ (mPa·s) denotes the viscosity at a number of spindle revolutions of x (rpm), ηy (mPa·s) denotes the viscosity at a number of spindle revolutions of y (rpm), which is larger than the number of spindle revolutions of x, their viscosity ratio is defined as ηx/ηy. The viscosity ratio $\eta_{1.5}/\eta_{3.0}$ of the viscosity $\eta_{1.5}$ at a number of spindle revolutions of 1.5 (rpm) to the viscosity $\eta_{3.0}$ at a number of spindle revolutions of 3.0 (rpm) is preferably $1.3 \leq \eta_{1.5}/\eta_{3.0} \leq 2.0$, more preferably $1.4 \leq \eta_{1.5}/\eta_{3.0} \leq 1.8$. Such a thixotropic fluid, which has a viscosity varying with the number of spindle revolutions, is often opaque, and the movement of inorganic particles is difficult to observe. The fluid for flow observation 30 containing the inorganic particles to be observed each having a planar surface, the dispersion medium to be observed, and the viscosity modifier can ensure the observation of the movement of the fluid containing the inorganic particles.

In the transmission cell 22 serving as a flow channel in the fluid observation apparatus 20, the ratio Lc/Dp of the flow channel width Lc (μm) of the transmission cell 22 to the particle size Dp (μm) of the inorganic particles to be observed in the fluid for flow observation 30 is preferably 5 or more and 200 or less. The particle size Dp refers to the median particle size (D50) as determined by a laser diffraction method. When a cross section perpendicular to the flow has different widths, the flow channel width Lc refers to a shorter width. When the width is not constant, the flow channel width Lc may be a representative flow channel width. The flow channel width Lc may be 1.0 μm or more and 1000 μm or less. The particle size Dp of the inorganic particles to be observed may be 0.2 μm or more and 5.0 μm or less.

In the transmission cell 22 in the fluid observation apparatus 20, the contact angle between the fluid for flow observation 30 and a wall surface of the flow channel through which the fluid for flow observation 30 is observed is preferably 50° or more and 100° or less, more preferably 60° or more and 95° or less. A contact angle of 80° or more and 100° or less, that is, approximately 90°, corresponds to the observation of the behavior of inorganic particles flowing near the center of the actual flow channel (for example, a mold in the gel casting process) through which the fluid passes, facilitating a better understanding of the behavior of the actual fluid. The wettability of the wall surface of the transmission cell 22 is preferably adjusted to the contact angle within these ranges. The contact angle can be determined by placing a drop of the fluid for flow observation 30 on the wall surface of the transmission cell 22 and measuring the angle between the wall surface and the surface of the droplet with a microscope. The wettability of the wall surface can be adjusted by the application of a water repellent or a hydrophilic agent. The material of the transmission cell 22 may be any transparent material, for example, glass, resin, such as acryl or PET, or silicone.

A method for observing a fluid by PIV will be described below. This method for observing a fluid can be performed with the fluid observation apparatus 20. The method for observing a fluid may include the steps of preparing a fluid for flow observation and capturing the particle image while the fluid for flow observation prepared flows. The preparation step includes the preparation of a fluid for flow observation 30, which contains inorganic particles to be observed each having a planar surface, a dispersion medium to be observed, and a viscosity modifier. The fluid for flow observation 30 to be prepared may be appropriately selected from those described above. In this preparation step, a simulated fluid for flow observation closely resembling the particle size of inorganic particles to be analyzed in a fluid for flow analysis and the viscosity of the fluid for flow analysis may be prepared as an example. For example, the fluid for flow analysis may be a slurry for use in the gel casting process and may contain inorganic particles to be analyzed (zirconia particles) and a dispersion medium to be analyzed (a mixture of aliphatic polyvalent ester and polybasic acid ester), and the fluid for flow observation 30 may contain inorganic particles to be observed (silicon carbide particles), a dispersion medium to be observed (a mixture of aliphatic polyvalent ester and polybasic acid ester), and a viscosity modifier.

In the capturing step, the fluid supply unit 21 is filled with the fluid for flow observation 30 thus prepared. While the fluid supply unit 21 is controlled to achieve a predetermined feed rate, the fluid for flow observation 30 passing through the transmission cell 22 is photographed with the digital video camera 23 or the digital camera 24. Images of inorganic particles in the fluid for flow observation 30 are captured while the fluid for flow observation 30 passing through the transmission cell 22 is irradiated with light from the photoirradiation units 26 and 27. The digital video camera 23 can capture reflected images of the inorganic particles while the inorganic particles are irradiated with light from the photoirradiation unit 26 and shaded images of the inorganic particles while the inorganic particles are irradiated with light from the photoirradiation unit 27. The digital camera 24 can capture shaded images of the inorganic particles while the inorganic particles are irradiated with light from the photoirradiation unit 26 and reflected images of inorganic particles while the inorganic particles are irradiated with light from the photoirradiation unit 27. In the fluid observation apparatus 20, photographing of slurry containing zirconia particles described above for use in the gel casting process with the digital video camera 23 only gives dark images, neither reflected nor shaded. In contrast, the fluid for flow observation 30 contains the planar inorganic particles 32 each having a planar surface allowing the control of translucency. The planar inorganic particles 32 facilitate the observation of reflected images. Thus, the movement of inorganic particles can be observed.

Three-dimensional flow analysis may be performed using physical properties obtained through fluid observation by PIV. The three-dimensional flow analysis can employ an existing method, such as the finite volume method, the finite element method, the finite difference method, the finite boundary method, or the particle method. Physical properties obtained from the observation of slurry for use in the gel casting process by PIV can be used in a fluid flow simulation to determine the optimum positions of, for example, the inlet of slurry and the outlet of air in a mold.

The present invention is not limited to the above embodiment. Various modifications may be made within the technical scope of the present invention.

EXAMPLES

Specific examples of manufacturing a fluid for flow observation will be described below as experimental examples.

Fluid to be Analyzed

A slurry for use in the gel casting process was prepared as a fluid for flow analysis to be analyzed. 100 parts by weight of zirconia particles (manufactured by Tosoh Co.) serving as inorganic particles to be analyzed, 20 parts by weight of a mixture of triacetin and an organic dibasic acid ester (at a weight ratio of 1:9) serving as a dispersion medium to be analyzed, and 3 parts by weight of a dispersing aid (a polycarboxylic acid copolymer) were mixed. The volume parts of the raw materials were 16 volume parts of the inorganic particles, 18 volume parts of the dispersion medium, and 3 volume parts of the dispersing aid. Table 1 shows the inorganic particles, the compounding ratio, the specific gravity (g/cm$^3$), and the volume concentration (% by volume) of the inorganic particles in the fluid to be analyzed. Table 1 also summarizes the details of Experimental Examples 1 to 3 described below, the viscosity (mPa·s) of the fluid to be analyzed, the viscosity ratio $\eta_{1.5}/\eta_{3.0}$ of the viscosity $\eta_{1.5}$ at a number of spindle revolutions of 1.5 (rpm) to the viscosity $\eta_{3.0}$ at a number of spindle revolutions of 3.0 (rpm), the contact angle (°), and PIV observation results.

carbide particles (manufactured by Superior Graphite) serving as inorganic particles to be observed, 75 parts by weight of a mixture of triacetin and an organic dibasic acid ester (at a weight ratio of 1:9) serving as a dispersion medium to be observed, and 10 parts by weight of a polycarboxylic acid copolymer serving as a viscosity modifier (dispersing aid) were mixed. The volume parts of the raw materials were 31

TABLE 1

| | Compounding ratio[1] | | | | | Viscosity (mPa · s) | | | | |
|---|---|---|---|---|---|---|---|---|---|---|
| | Inorganic particles | Inorganic particles | Dispersion medium | Dispersing aid | Binder | Specific gravity g/cm³ | Concentration Vol % | Number of revolutions 1.5 rpm | Number of revolutions 3.0 rpm | Viscosity ratio[2] | Contact angle[3] (°) | PIV observation[4] |
| Fluid to be analyzed | ZrO₂ | 100 g 16 cm³ | 20 g 18 cm³ | 3 g 3 cm³ | — — | 3.3 | 43 | 12000 | 8000 | 1.5 | 83 63 | No |
| Experimental Example 1 | SiC | 100 g 31 cm³ | 50 g 45 cm³ | 4.2 g 4 cm³ | — — | 1.9 | 38 | 12000 | 9000 | 1.3 | 83 65 | Yes |
| Experimental Example 2 | SiC | 100 g 31 cm³ | 77.8 g 71 cm³ | 6 g 6 cm³ | 1.1 g 1 cm³ | 1.7 | 28 | 16000 | 8000 | 2.0 | 81 71 | Yes |
| Experimental Example 3 | SiC | 100 g 31 cm³ | 75 g 68 cm³ | 10 g 10 cm³ | — — | 1.7 | 28 | 128000 | 60000 | 2.1 | Unmeasurable Unmeasurable | Yes |

[1] Upper: weight ratio, Lower: volume ratio
[2] Viscosity ratio: ratio $\eta_{1.5}/\eta_{3.0}$ of viscosity $\eta_{1.5}$ at 1.5 rpm to viscosity $\eta_{3.0}$ at 3.0 rpm
[3] Upper: a cell wall coated with a fluorine mold-release agent, Lower: a cell wall coated with a silicone mold-release agent
[4] Yes: inorganic particles were observed by PIV, No: inorganic particles were not observed by PIV Experimental Example 1

A slurry containing inorganic particles was prepared as a fluid for flow observation so as to closely resemble a fluid for flow analysis. 100 parts by weight of silicon carbide particles (manufactured by Superior Graphite) serving as inorganic particles to be observed, 50 parts by weight of a mixture of triacetin and an organic dibasic acid ester (at a weight ratio of 1:9) serving as a dispersion medium to be observed, and 4.2 parts by weight of a dispersing aid (a polymerized alkylammonium salt compound having an acid group) serving as a viscosity modifier were mixed. The volume parts of the raw materials were 31 volume parts of the inorganic particles, 45 volume parts of the dispersion medium, and 4 volume parts of the dispersing aid.

Experimental Example 2

A slurry containing inorganic particles was prepared as a fluid for flow observation so as to closely resemble a fluid for flow analysis. 100 parts by weight of silicon carbide particles (manufactured by Superior Graphite) serving as inorganic particles to be observed, 77.8 parts by weight of a mixture of triacetin and an organic dibasic acid ester (at a weight ratio of 1:9) serving as a dispersion medium to be observed, 6 parts by weight of a dispersing aid (a polymerized alkylammonium salt compound having an acid group) serving as a viscosity modifier, and 1.1 parts by weight of polyvinyl acetal resin (a molecular weight of approximately 23,000, a butyral content of 74% by mole) serving as a viscosity modifier (binder) were mixed. The volume parts of the raw materials were 31 volume parts of the inorganic particle, 71 volume parts of the dispersion medium, 6 volume parts of the dispersing aid, and 1 volume parts of the binder.

Experimental Example 3

A slurry containing inorganic particles was prepared as a fluid for flow observation. 100 parts by weight of silicon volume parts of the inorganic particles, 68 volume parts of the dispersion medium, and 10 volume parts of the dispersing aid.

Measurement of Particle Size Distribution

The particle size distribution of the zirconia particles and the silicon carbide particles used as inorganic particles was measured. The particle size of inorganic particles was determined as a median size (D50) using water as a dispersion medium with a laser diffraction/scattering particle size distribution analyzer LA-700 manufactured by HORIBA Ltd. Both the zirconia particles and the silicon carbide particles had a median size (D50) of 0.5 μm.

Observation of Inorganic Particles

Figure 2:
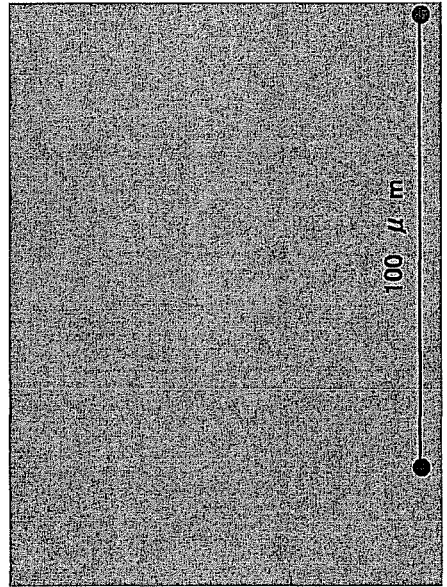
FIG. 2 shows SEM photographs and optical photomicrographs of inorganic particles.
Figure 2:
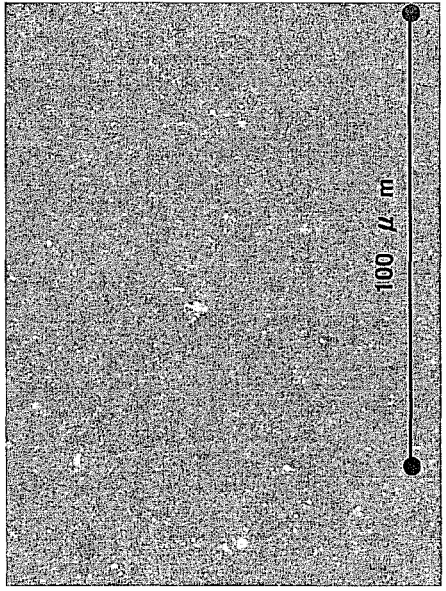
Figure 2:
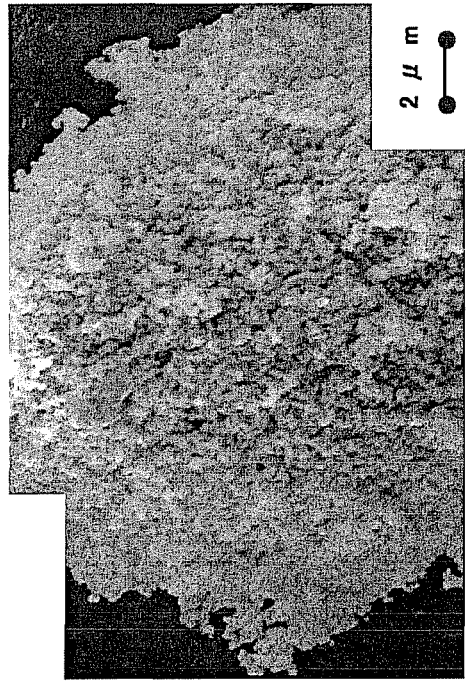
Figure 2:
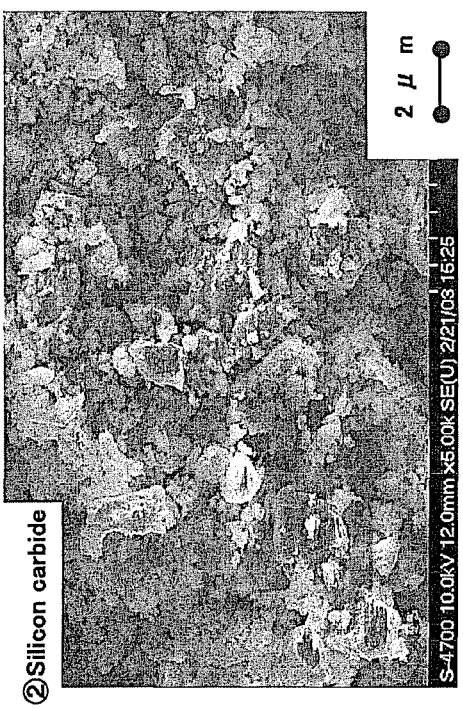

The zirconia particles and the silicon carbide particles used as inorganic particles were observed. The inorganic particles were observed with an electron microscope (SEM) and an optical microscope. The SEM observation was performed with an electron microscope (S-3000N manufactured by Hitachi High-Technologies Co.) at a magnification of 5,000. FIG. 2 shows SEM photographs and optical photomicrographs of the inorganic particles. The photograph shows that the zirconia particles were generally spherical particles. The particle size distribution was narrow, and the particle sizes were substantially the same. The silicon carbide particles contained generally spherical particles and a relatively large number of particles each having a planar surface. The silicon carbide particles also contained relatively large particles having a size of approximately 2 μm. In the observation of slurry under incident light, the zirconia particles were difficult to observe in the slurry, whereas in the slurry containing the silicon carbide particles particle images probably of particles each having a planar surface (flat particles) were clearly observed.

Measurement of Viscosity

Figure 3:
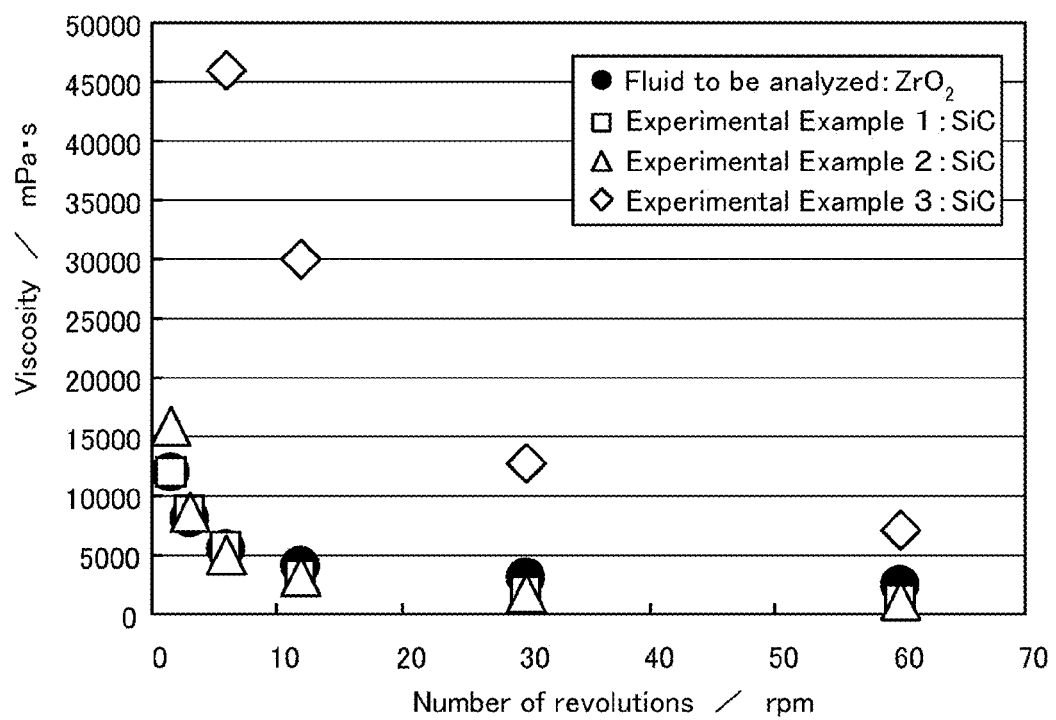
FIG. 3 is a graph illustrating the viscosities of samples as a function of the number of revolutions.

The viscosities (mPa·s) of the fluids to be analyzed and the fluids for flow observation according to Experimental Examples 1 to 3 were measured with a B type viscometer (manufactured by Brookfield Engineering Laboratories, Inc., a main body: LVT, a cylindrical spindle: LV No. 4) at numbers of revolutions of 1.5, 3, 6, 12, 30, and 60 rpm. Table 2 and FIG. 3 show the viscosities of samples as a function of the number of revolutions. All the samples were non-Newtonian fluids, the viscosity of which varied with the number of revolutions. The fluids for flow observation according to Experimental Examples 1 and 2 had a viscosity close to the viscosity of the fluid to be analyzed.

TABLE 2

| | Viscosity (mPa · s) | | | | | |
|---|---|---|---|---|---|---|
| | Number of revolutions 1.5 rpm | Number of revolutions 3.0 rpm | Number of revolutions 6.0 rpm | Number of revolutions 12 rpm | Number of revolutions 30 rpm | Number of revolutions 60 rpm |
| Fluid to be analyzed | 12000 | 8000 | 5500 | 4000 | 3000 | 2350 |
| Experimental Example 1 | 12000 | 9000 | 5500 | 3250 | 1800 | 1150 |
| Experimental Example 2 | 16000 | 8000 | 4500 | 3000 | 1500 | 950 |
| Experimental Example 3 | 128000 | 60000 | 46000 | 30000 | 12800 | 7050 |

Measurement of Contact Angle

The contact angles (°) of the fluids to be analyzed and the fluids for flow observation according to Experimental Examples 1 to 3 were measured. After an observation window of the transmission cell was coated with a mold-release agent serving as a water repellent, a sample droplet was placed on the observation window. The contact angle of the sample droplet was measured with a microscope. An F- or Si-containing compound was appropriately used as the mold-release agent. In this measurement, a first mold-release agent (a fluorine mold-release agent) and a second mold-release agent (a silicone mold-release agent) were used. The measurement showed that the fluids for flow observation according to Experimental Examples 1 and 2 had a contact angle close to the contact angle of the fluid to be analyzed. The contact angle could not be measured in Experimental Example 3 because the droplet became creamy. The first mold-release agent was found to be preferred because a contact angle of approximately 90° corresponds to the observation of the behavior of inorganic particles flowing near the center of the actual flow channel through which the fluid passes.

PIV Observation

Figure 4:
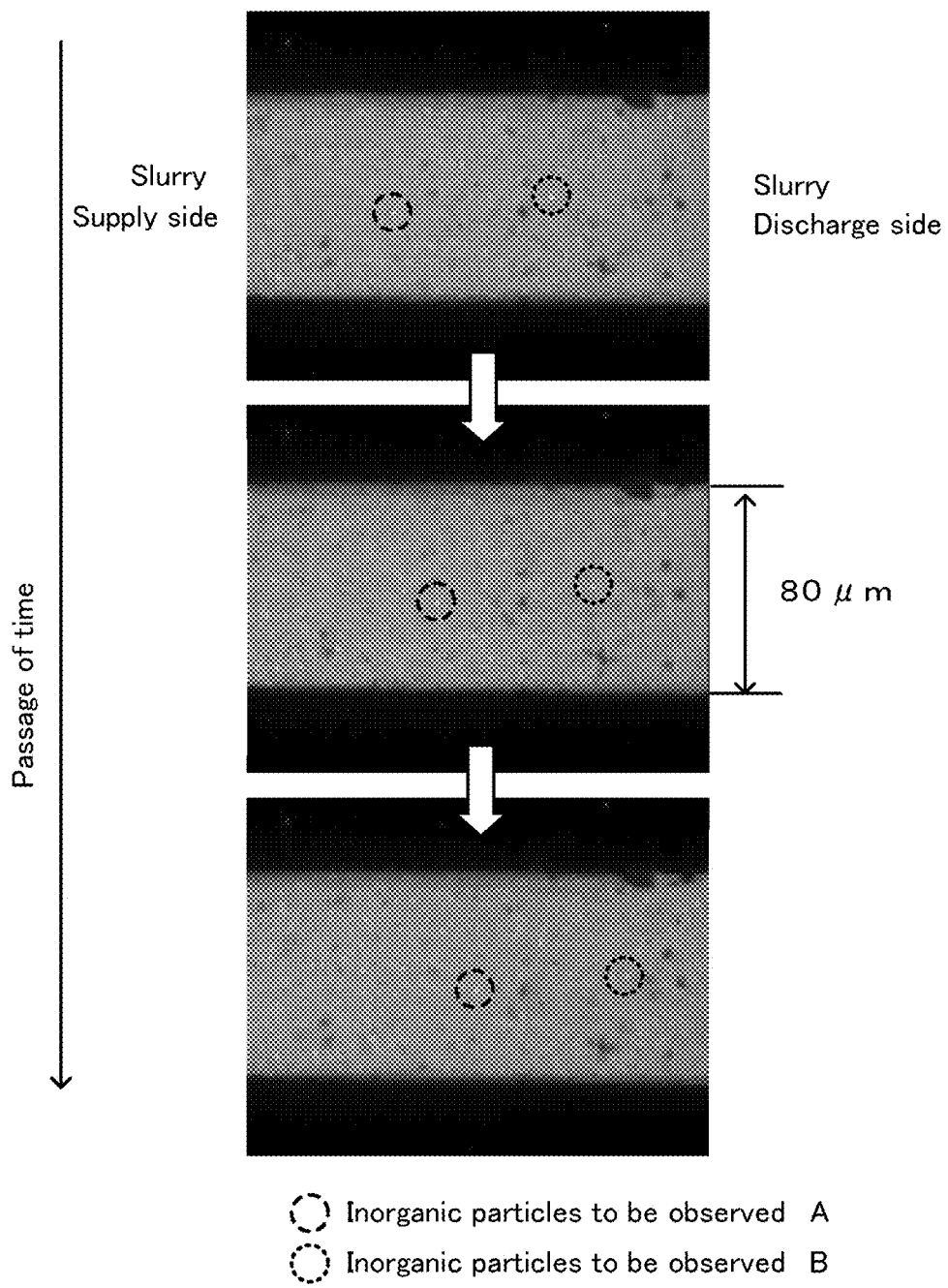
FIG. 4 shows PIV observations of Experimental Example 1.

The PIV observation of the fluids to be analyzed and the fluids for flow observation according to Experimental Examples 1 to 3 were performed with the fluid observation apparatus 20. In the PIV observation, the transmission cell 22 was made of acryl, and the first mold-release agent was applied to the wall surface on which the fluid flowed. The transmission cell 22 had a rectangular flow channel and a flow channel width Lc of 80 μm. In the fluid observation apparatus 20, the feed rate of the fluid for flow observation was 0.012 mm³/min, and still pictures were continuously taken with the digital camera. FIG. 4 shows PIV observations of Experimental Example 1. As shown in FIG. 4, the movement of inorganic particles could be successfully observed. Even at a depth of focus deeper than the wall surface of the transmission cell 22, that is, at a more centered position of the fluid for flow observation, the movement of inorganic particles could be successfully observed.

The present application claims the benefit of the priority from Japanese Patent Application No. 2010-029043 filed on Feb. 12, 2010, the entire contents of which are incorporated herein by reference.

What is claimed is:

1. A method for observing the movement of a fluid passing through a flow channel by particle image velocimetry (PIV), comprising
a capturing step of capturing an image of inorganic particles in a fluid for flow observation by irradiating the fluid for flow observation passing through a flow channel with light, the fluid for flow observation containing inorganic particles to be observed each having a planar surface, a dispersion medium to be observed, and a viscosity modifier.

2. The method for observing a fluid according to claim 1, wherein the volume percentage of the inorganic particles to be observed is 20% by volume or more and 40% by volume or less.

3. The method for observing a fluid according to claim 1, wherein the fluid for flow observation has a viscosity ratio $\eta_{1.5}/\eta_{3.0}$ in the range of $1.3 \leq \eta_{1.5}/\eta_{3.0} \leq 2.0$, the $\eta_{1.5}$ being a viscosity measured with a B type viscometer at a number of revolutions of 1.5 rpm, the $\eta_{3.0}$ being a viscosity measured with the B type viscometer at a number of revolutions of 3.0 rpm.

4. The method for observing a fluid according to claim 1, wherein the ratio Lc/Dp of the width Lc (μm) of the flow channel to the particle size Dp (μm) of the inorganic particles to be observed contained in the fluid for flow observation is 5 or more and 200 or less.

5. The method for observing a fluid according to claim 1, wherein a wall surface of the flow channel has a contact angle with the fluid for flow observation of 50° or more and 100° or less.

6. The method for observing a fluid according to claim 1, wherein the capturing step includes capturing an image of inorganic particles in a fluid for flow observation by using a simulated fluid for flow observation and irradiating the simulated fluid for flow observation with light, the simulated fluid for flow observation containing the inorganic particles to be observed each having a planar surface, the dispersion medium to be observed, and the viscosity modifier, the simulated fluid for flow observation closely resembling the particle size of inorganic particles to be analyzed and the viscosity of a fluid for flow analysis, the fluid for flow analysis containing the inorganic particles to be analyzed and a dispersion medium to be analyzed.

7. The method for observing a fluid according to claim 6, wherein the inorganic particles to be analyzed are zirconia particles, and the inorganic particles to be observed are silicon carbide particles.

8. The method for observing a fluid according to claim 6, wherein the volume percentage of the inorganic particles to be observed contained in the fluid for flow observation is smaller than the volume percentage of the inorganic particles to be analyzed contained in the fluid for flow analysis.

9. The method for observing a fluid according to claim 1, wherein the dispersion medium to be observed is a resin curable under predetermined conditions.

10. A fluid for flow observation to be observed by PIV, comprising inorganic particles to be observed each having a planar surface, a dispersion medium to be observed, and a viscosity modifier wherein the fluid for flow observation is a simulated fluid for the fluid for flow analysis, the simulated fluid closely resembling the particle size of inorganic particles to be analyzed and the viscosity of the fluid for flow analysis, the fluid for flow analysis containing the inorganic particles to be analyzed and a dispersion medium to be analyzed, the simulated fluid containing the inorganic particles to be observed each having a planar surface, the dispersion medium to be observed, and the viscosity modifier.

11. The method for observing a fluid according to claim 1, wherein the fluid is a liquid.

12. The method for observing a fluid according to claim 11, wherein the liquid is a ceramic slurry.

13. The method for observing a fluid according to claim 1, wherein the viscosity modifier is selected from the group consisting of a dispersing aid and a binder.

14. The method for observing a fluid according to claim 13, wherein the dispersing aid is selected from the group consisting of sorbitan fatty acid esters, polycarboxylic acid copolymers, polymerized phosphate ester (salt) compounds, polymerized alkylammonium salt compounds having an acid group, and sodium alkylbenzenesulfonate.

15. The method for observing a fluid according to claim 13, wherein the binder is selected from the group consisting of cellulose derivatives, starch, polyvinyl alcohol, polyethylene glycol, butyral resin, acrylic resin, polyamide resin and isocyanates.

* * * * *